(12) United States Patent  
Sakabe (10) Patent No.: US 7,460,644 B2  
(45) Date of Patent: Dec. 2, 2008

(54) X-RAY GENERATING METHOD AND X-RAY GENERATING APPARATUS

(75) Inventor: Noriyoshi Sakabe, Tsukuba (JP)

(73) Assignees: Noriyoshi Sakabe, Tsukuba (JP); Kiwako Sakabe, Tuskuba (JP)

( * ) Notice: Subject to any disclaimer, the term of this patent is extended or adjusted under 35 U.S.C. 154(b) by 71 days.

(21) Appl. No.: 11/657,557

(22) Filed: Jan. 25, 2007

(65) Prior Publication Data

US 2007/0223655 A1    Sep. 27, 2007

(30) Foreign Application Priority Data

Mar. 22, 2006  (JP) .............................. 2006-078890  
Jun. 9, 2006    (JP) .............................. 2006-160780

(51) Int. Cl.  
*G21G 4/00*  (2006.01)

(52) U.S. Cl. ........................................ 378/119; 378/84  
(58) Field of Classification Search ................... 378/84, 378/85, 119, 82  
See application file for complete search history.

(56) References Cited

U.S. PATENT DOCUMENTS

2004/0218718 A1*  11/2004  Freudenberger et al. ...... 378/82

* cited by examiner

*Primary Examiner*—Courtney Thomas  
(74) *Attorney, Agent, or Firm*—Oliff & Berridge, PLC

(57) ABSTRACT

An energy beam is irradiated onto a target from an energy beam source, thereby generating an X-ray with an irradiating area to be irradiated onto an object. Then, the X-ray is introduced into a spectrometer, thereby generating an X-ray with parallelism through the selection of wavelength and wavelength range.

30 Claims, 3 Drawing Sheets

X-RAY GENERATING METHOD AND X-RAY GENERATING APPARATUS

BACKGROUND

1. Field of the Invention

This invention relates to an X-ray generating method and an X-ray generating apparatus, which are particularly usable for medical treatment.

2. Description of the Background Art

In X-ray photography for medical use, a given X-ray tube is employed, and an X-ray is irradiated onto an object from the X-ray tube so that the X-ray through the object is photographed and detected at a detecting section such as an X-ray sensitivity film, and the thus obtained image is analyzed for the medical use.

For example, an X-ray generated from a conventional X-ray tube has an effective focal spot with 1 mm×1 mm. When the irradiated surface area on the object is 10 cm×10 cm, it is necessary to enlarge the x-ray size to 10 cm×10 cm. In this case, the brightness of the X-ray is weakened by a ratio of (1 mm×1 mm)/(100 mm×100 mm). In other words, when the conventional X-ray tube is employed, the brightness of the X-ray is decreased to $10^{-4}$ times as the initial brightness of the X-ray from the X-ray tube.

Moreover, in the medical use of the conventional X-ray tube, some components with unnecessary wavelength would be cut off with some filters. Thus the unnecessary components can not be removed sufficiently.

In order to photograph a moving object such as coronary artery in the medical use at high resolution, it is required to irradiate a high intensity X-ray with excellent parallelism and high power onto the moving object in a short period of time. In the conventional X-ray tube, however, the brightness of the X-ray is remarkably decreased when the X-ray is irradiated onto the moving object and the parallelism of the X-ray can not be realized sufficiently. In this point of view, the medical use of the conventional X-ray tube is restricted and thus, can not be employed for wide medical use.

SUMMERY OF THE INVENTION

It is an object of the present invention, in view of the conventional problems, to provide an X-ray generating method and an X-ray generating apparatus which can generate a high intensity X-ray with high parallelism and high power.

Means for Solving the Problem:

In order to achieve the object, this invention relates to a method for generating an X-ray, comprising the steps of:

irradiating an energy beam onto a target from an energy beam source, thereby generating an X-ray with an irradiating area to be irradiated onto an object, and introducing said X-ray into a spectrometer, thereby generating an X-ray with parallelism through the selection of wavelength and wavelength range.

Also, this invention relates to an apparatus for generating an X-ray, comprising:

a target for generating an X-ray through the irradiation of an energy beam, an energy beam source for generating said energy beam to generate said X-ray so as to have an irradiating area to be irradiated onto an object and a spectrometer for selecting wavelength and wavelength range of said X-ray through the introduction of said X-ray so as to generate an X-ray with parallelism from said X-ray.

In the present invention, the target is prepared different from the conventional X-ray tube, and the energy beam is irradiated onto the target. Therefore, if the irradiating intensity and irradiating cross section of the energy beam are controlled for the target, the output intensity and brightness of the thus obtained X-ray can be enhanced easily. In this point of view, the output intensity and brightness of the X-ray can be varied in dependent on the object.

In the present invention, the X-ray, which is generated from the target, is introduced into the spectrometer. Therefore, the X-ray can be rendered parallelism and the irradiating surface of the X-ray can be increased almost equal to the irradiating surface of the object. Moreover, since the X-ray is introduced into the spectrometer, the wavelength range of the X-ray can be restricted within a given range after the spectrometer.

In an aspect of the present invention, the spectrometer includes a crystal plate. In this case, the crystal plate may be two or more crystal plates which are to be combined. At least one of the crystal plates may function as an X-ray surface reflective type crystal plate. At least one of the crystal plates may function as an X-ray transmission type (Laue type) crystal plate. According to this aspect, the intended X-ray with parallelism can be obtained easily. Moreover, if the combination of the crystal plates is varied, the X-ray with the parallelism can be rendered monochromatic.

Moreover, the crystal plate is made of a cubic crystal such as LiF so as to function as perpendicularly arranged two crystal plates. In this case, since at least two identical reflection planes orthogonal to one another are included in the cubic crystal, the X-ray is reflected at the two reflection planes by an reflective angle of a when the reflective angle is defined as $\alpha$. Therefore, since the cubic crystal plate can functions as the two (reflective) crystal plates, the intended X-ray with the parallelism can be obtained under the condition that the number of crystal plate can be decreased. In this case, the X-ray with the parallelism can be rendered monochromatic by the subsequent crystal plate.

All of the crystal plates can be X-ray surface reflective type crystal plates or X-ray transmission type crystal plates. Also, one or more of the X-ray surface reflective type crystal plates may be combined with one or more of the X-ray transmission type crystal plates.

In order to develop the large cross section of the X-ray, the crystal plate(s) may be made of (a) material(s) selected from the group consisting of silicon, graphite, germanium and quartz, in addition to the crystal plate made of LiF.

The crystal plate may be made of a multilayered reflective plate for X-ray. The multilayered reflective plate may be configured such that two or more layers are laminated periodically in order to develop the brightness of the X-ray and the intended monochromatic X-ray can be obtained within a given width by means of X-ray diffraction. In this case, the relation between the wavelength and reflective angle are determined on the periodicity of the multilayered reflective plate. Then, if the layer number and periodicity of the multilayered reflective plate are varied, the width of the reflective X-ray wavelength can be also varied.

As described above, since according to the present invention a high intensity X-ray with high parallelism and large cross section which is similar size to the object can be generated. Instead of the conventional X-ray tube, the X-ray source can be preferably usable for medical use. With the X-ray source according to the present invention, the X-ray photography for the moving object such as coronary artery can be realized at high special resolution in high speed because the intended X-ray can be irradiated onto the moving object in a short period of time which is originated from the high power and high parallelism of the X-ray from the X-ray source.

For example, if nonionic iodine is injected as contrast agent from a vein of an object and the images in the vicinity of the iodine absorption edge (at the front of the absorption edge and the rear of the absorption edge), which is represented as 33,17 KeV at energy and as 0.3738 Å at wavelength, are photographed by the X-ray from the X-ray source of the present invention, the blood vessel of the object can be imaged clearly. As of now, the imaging technique can be performed by utilizing a high energy synchrotron radiation (SR) (e.g., SR of 6 GeV ring at KEK in Japan or that of 8 GeV ring at SPring-8 in Japan). However, it is difficult to establish the high energy SR ring in a hospital, namely, medical field. In this point of view, the imaging technique can not be established yet, but the present invention can realize the imaging technique by utilizing the high intensity X-ray with high parallelism and high power.

The reason to generate such an X-ray with high parallelism by introducing the X-ray into the spectrometer is described as follows. When an X-ray is introduced into a spectrometer such as a crystal or a X-ray multilayered film, the X-ray is diffracted in accordance with the equation of $2d \sin \theta = n\lambda$ (Bragg's equation). Herein, the reference character "d" designates a spacing in the crystal or the X-ray multilayered film, and the reference character "$\theta$" designates incident and diffraction angles of the X-ray for the reflection plane, and the reference character "$\lambda$" designates a wavelength of the X-ray, and the reference character "n" designates an integer (order of harmonics). Spacing "d" is defined by Miller index (hkl) and crystal lattice parameters. Thus, the wavelength "$\lambda$" can be determined by the given incident angle "$\theta$". As apparent from the equation, the harmonic wavelength cannot be removed by the diffraction. For example, if the X-ray is a monochromatic X-ray and the shape of which is a straight line, the monochromatic X-ray can be diffracted for the direction of angle $\theta$ according to the Bragg's equation and the straight line shape is kept after the diffraction. In this case, all the diffracted X-rays in the straight line must be an X-ray with parallelism. In contrast, the monochromatic X-ray and the shape of which is a very broad line can be diffracted to many different directions according to the incident beam directions which still keep the $\theta$ from the diffraction plane. In this case, the thus obtained X-ray can not be an X-ray with parallelism. By disposing a similar crystal (second crystal) such that the reflection plane of the second crystal can be perpendicular to the previous crystal and diffracting the X-ray with non-parallelism at the reflection plane, then, only the X-ray with parallelism part can be diffracted and the diffracted X-ray forms with parallelism. In this way, even though the X-ray is diffracted for some directions containing the $\theta$ direction at the crystal, etc., the X-ray through the crystals can be an X-ray with parallelism.

In another aspect of the present invention, the X-ray is transmitted through at least one of an absorptive plate and a slit so as to remove components with unnecessary wavelength of the X-ray before the X-ray is introduced into the spectrometer. In this case, the lower energy components of the X-ray can be removed effectively and efficiently. For example, the absorptive plate can be made of an Al plate. The use of the absorptive plate can reduce unnecessary heat load for the spectrometer.

Although the thickness of the Al plate can be determined by many parameters such as the intensity and hardness of the X-ray generated from the target and object to be irradiated, for example, the thickness of the Al plate may be defined within a range of 1-10 mm.

As described above, if the two or more reflective type crystal plates are combined so that their respective reflection plane are orthogonal to one another, the intended X-ray with the parallelism can be obtained. Then, the X-ray with the parallelism can be rendered monochromatic by the subsequent crystal plate because the unnecessary wavelength components can be removed. The reflective type crystal plates may be made of the same material or respective different materials.

In a still another aspect of the present invention, a surface portion of the target to which the energy beam is irradiated is partially melted or completely melted. In the former case, since the intensity of the energy beam can be developed enough to increase the temperature of the target in the vicinity of the melting point thereof, the intensity of the intended X-ray can be also enhanced. In this case, a film may be formed on the surface of the target so as to decrease the evaporation velocity thereof by the energy beam. The film is made of a material selected from the group consisting of BN, graphite, diamond, Be, $Al_2O_3$.

In the latter case, since the intensity of the energy beam can be developed enough to increase the temperature of the target in the vicinity of the melting point thereof and the irradiating point of the target is melted subsequently commensurate with the shift of the energy beam by the anticathode rotation, the intensity of the intended X-ray can be also enhanced and the target surface can be flattened through the melting of the target so that the target surface can be maintained flat during the irradiation of the energy beam. As a result, the intended X-ray can be obtained without the absorption of the target roughness so that the high intensity of the X-ray can be maintained for a long time.

In a further aspect of the present invention, the target is a rotating anticathode and the energy beam is irradiated onto a portion of the anticathode which is against the centrifugal force originated from the rotation of the anticathode. In this case, even though the target is melted partially from the irradiation of the energy beams, the outer splash of the melting area of the target can be repressed effectively and efficiently. Also, since the irradiating position of the energy beam can be shifted, the intended X-ray can be generated constantly in high intensity.

The target may be a stationary type target because the rotating anticathode has the complicated structure and becomes expensive.

The rotating anticathode may have a cylindrical portion which is provided along the periphery of the rotating anticathode so that the energy beams are irradiated onto the inner wall of the cylindrical portion of the anticathode. In this case, the target melting occurs at the inner wall of the cylindrical portion of the rotating anticathode, the outer splash of the melting area of the rotating anticathode due to the energy beam irradiation can be repressed more effectively.

The side wall of the cylindrical portion of the rotating anticathode can be inclined inwardly so that the outer splash of the melting area of the rotating anticathode due to the energy beam irradiation can be repressed more effectively. In contrast, the side wall of the cylindrical portion of the rotating anticathode can be inclined outwardly so that the intended X-ray can be taken easily out of the rotating anticathode under the condition that the outer splash of the meting area of the rotating anticathode can be repressed.

Then, the irradiating area of the energy beam in the rotating anticathode can be formed in a V-shaped ditch or a U-shaped ditch so that the outer splash of the melting area of the target due to the energy beam irradiation can be repressed effectively. In this case, the V-shaped irradiating area or the U-shaped irradiating area can be formed in such a shape as the centrifugal force affects the melting area of the target during the rotation of the rotating anticathode. In this case, the target surface roughness of the rotating anticathode can be repressed effectively so that the intended X-ray can be generated constantly in high intensity.

In a still further aspect of the present invention, the area around the energy beam irradiating area in the target is made of a material with higher melting point and/or higher thermal conductivity than the target itself. In this case, the cooling efficiency of the target can be enhanced entirely and the deformation of the target can be repressed efficiently so that the intended X-ray can be generated constantly in high intensity over a prolonged period of time.

Concretely, the target for generating the intended X-ray is configured such that a cooling water is flowed along the backside of the energy beam irradiating area of the target for the constant cooling of the target. However, if the intensity of the energy beams is set too high and the irradiating period of the energy beams is set too long, the energy beam may penetrate though the target so that the cooling water is leaked to the X-ray generating side, thereby rendering the X-ray generating apparatus with the rotating anticathode malfunction.

In this point of view, the target can be a double structured target which is composed of the target metal to emit intended characteristic X-ray and the high melting point and/or high thermal conductivity substance which is provided at the backside of the target so that the energy beam is irradiated onto the target and the cooling medium such as a cooling water is flowed along the backside of the substance. In this case, the energy beams can not penetrate through the target so that the cooling medium can not be leaked to the X-ray generating side, originated from the large heat resistance due to the high melting point of the substance and the large cooling performance due to the high thermal conductivity of the substance.

According to the present invention can be provided an X-ray generating method and an X-ray generating apparatus which can generate a high intensity X-ray with high parallelism and high power and which can be utilized in an industrial field such as nano-machine fabrication and integral circuit design or a laboratory field requiring the large surface and parallelism of X-ray such as X-ray topography and imaging.

BRIEF DESCRIPTION OF THE DRAWINGS

For better understanding of the present invention, reference is made to the attached drawings, wherein.

DESCRIPTION OF THE PREFERRED EMBODIMENTS

This invention will be described in detail with reference to the accompanying drawings.

Figure 1:
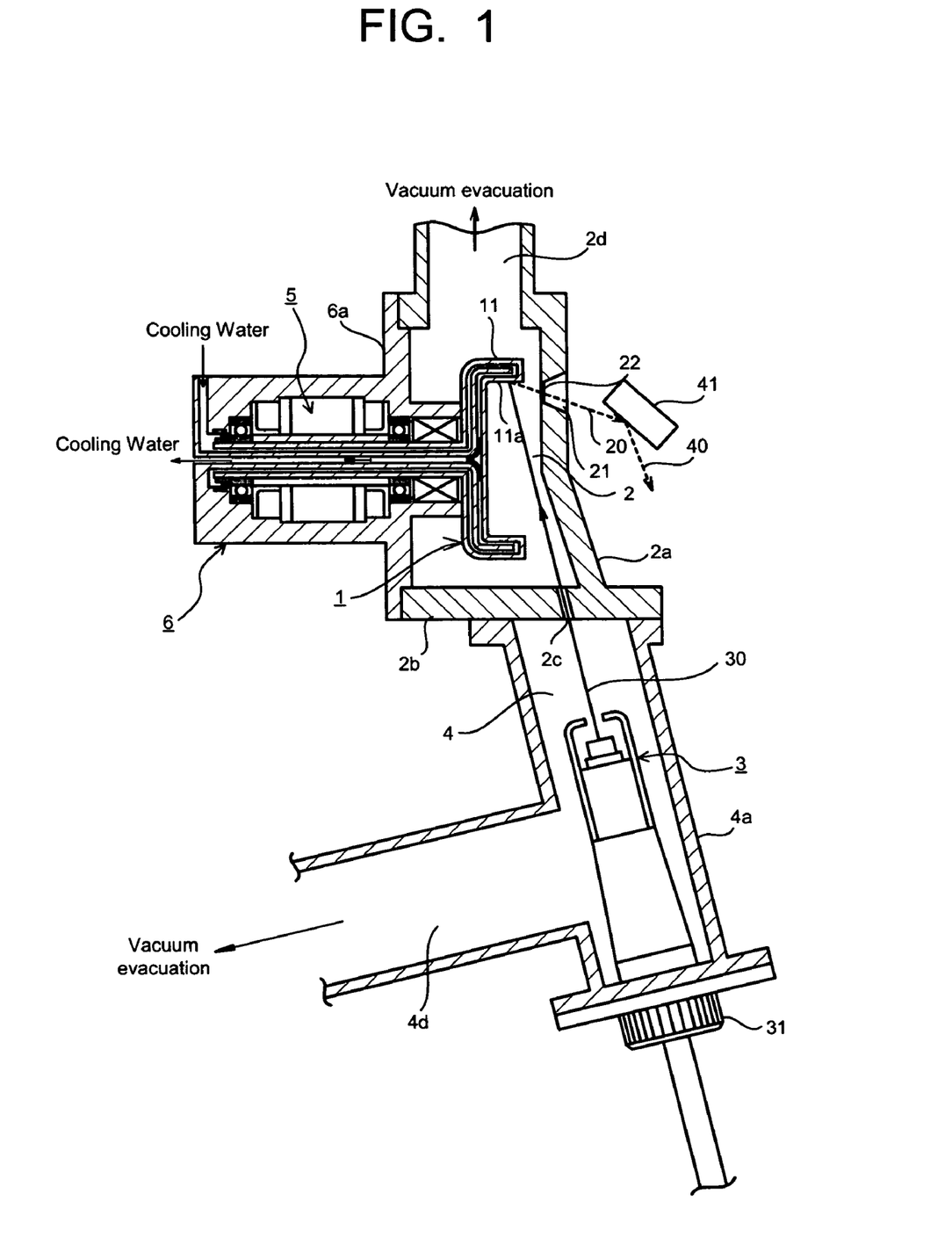
FIG. 1 is across sectional view illustrating an X-ray generating apparatus according to the present invention.
Figure 2:
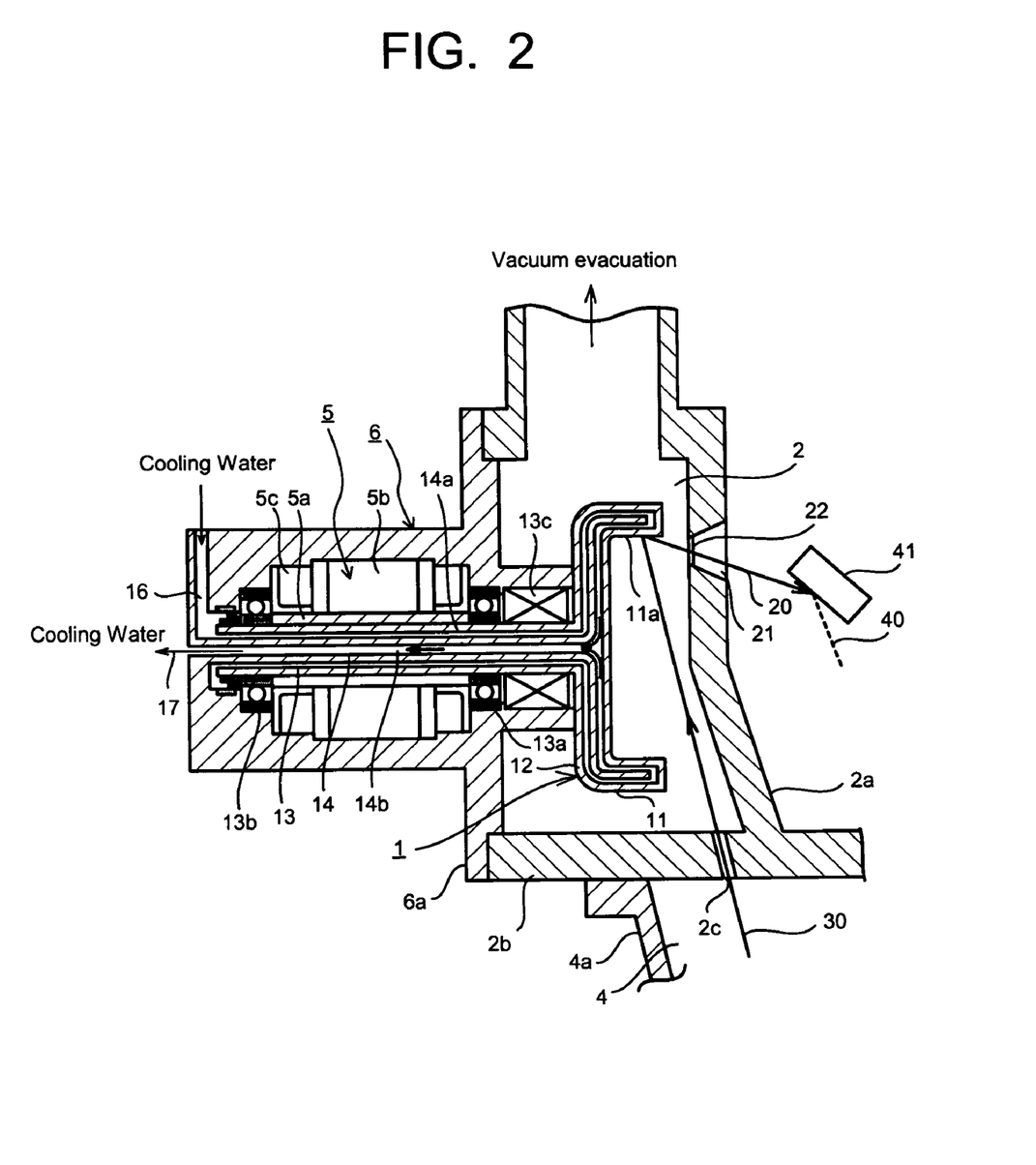
FIG. 2 is an enlarged cross sectional view illustrating a part of the X-ray generating apparatus illustrated in FIG. 1.

FIG. 1 is a cross sectional view illustrating an X-ray generating apparatus according to the present invention, and FIG. 2 is an enlarged cross sectional view illustrating a part of the X-ray generating apparatus illustrated in FIG. 1.

The X-ray generating apparatus includes an anticathode chamber 2 for accommodating a rotating anticathode 1, a cathode chamber 4 for accommodating a cathode 3 and a rotation driving chamber 6 for accommodating a driving motor 5 for rotating the anticathode 1 which are located in the vicinity of one another and separated from one another by air-tight members 2a, 4a and 6a in FIGS. 1 and 2. At a separating wall 2b for separating the anticathode chamber 2 and the cathode chamber 4 is formed a small hole 2c for passing electron beams 30 to be emitted from the cathode 3 through the separating wall 2b. Then, at the anticathode chamber 2 and the cathode chamber 4 are provided vacuum outlets 2d and 4d, respectively to which vacuum pumps (not shown) are connected. Herein, a tube may be disposed at the hole 2c.

In these figures, although the electron beams 30 is illustrated linearly, the electron beam 30 can be illustrated widely so as to realize a wider irradiating surface for an object. A diode electron beam source or a triode electron beam source is also available as the electron beam source 3 as described below. In this point of view, although it should be that the electron beams 30 is illustrated wider, in this embodiment, the electron beams 30 is illustrated linearly for simplicity. Therefore, the small hole 2c is required to have a size wide enough to pass the electron beams 30 therethrough.

The rotating anticathode 1 includes a cylindrical portion 11a made of metal to emit intended characteristic X-ray such as Cu, Mo, W or the like, a circular plate 12 formed so as to close the one opening of the cylindrical portion 11, and a rotating shaft 13 with a center shaft shared with the cylindrical portion 11 and the circular plate 12 which are integrally formed. The interiors of the cylindrical portion 11, the circular plate 12 and the rotating shaft 13 are formed a cavity so that a cooling water can be flowed in the interiors thereof. The electron beam is irradiated onto the inner wall 11a of the cylindrical portion 11.

The rotating shaft 13 is supported rotatably by a pair of bearings 13a and 13b which are provided in the rotation driving chamber 6. The rotator 5c of the driving motor 5 is provided at the periphery of the rotating shaft 13, and the stationary inductor 5b to rotate the rotator 5c cover the rotator 5c. A cylinder type motor shaft connected to rotator 5c is tightly fixed to the rotating shaft 13 which is attached to the air-tight seal 13c in the rotation driving chamber 6.

At the root of the rotating shaft 13 near the circular plate 12 is provided a rotating shaft-sealing member 13c such as ferrofluid seal for maintaining the interior of the anticathode chamber 2 in vacuum by arranging the rotating shaft 13 and the air-tight vessel 6a under air-tight condition.

In the rotating anticathode 1 is inserted a stationary separating member 14 for flowing the cooling water along the inner wall of the electron beam irradiating portion 1a. The stationary separating member 14 is formed in a cylindrical shape, enlarged along the shape of the circular shape 12 and elongated short of the inner wall of the cylindrical portion 11.

In other words, the stationary separating member 14 divides the interior space of the rotating anticathode 1 so as to be a double tube structure. The outer tube 14a of the double tube structure is communicated with a cooling water inlet 16. Herein, an axial sealing member 14 is provided at the left-side periphery of the rotating shaft 13 so that the cooling water, which is introduced from the inlet 16, is introduced into the outer tube 14a of the double tube structure so as not to be leaked to the accommodating space where the bearings 13a, 13b and the driving motor 5 are provided.

The cooling water, which is introduced from the inlet 16, is flowed in the outer tube 14a of the double tube structure, returned from the inner wall of the cylindrical portion 11 and flowed in the inner tube 14b of the double tube structure. In this case, the inner wall of the electron beam irradiating portion 11a is cooled by the cooling water, and the remnant cooling water is flowed in the inner tube 14b and discharged from the outlet 17.

At the air-tight member 2a in the vicinity of the electron beam irradiating portion 11a of the rotating anticathode 1 is provided an X-ray window 21 for taking out an X-ray 20 generated by the irradiation of the electron beams 30 onto the electron beam irradiating portion 11a. At the X-ray window 21 is provided an X-ray transmitting film 22 made of a material which can pass the X-ray therethrough such as Be, Al so that the intended X-ray can be taken out of the apparatus with maintaining the vacuum condition of the anticathode chamber 2. In this embodiment, since the X-ray 20 has a large cross section, almost equal to the effective irradiation surface onto the object, the X-ray window 21 is formed wide enough to pass the wider X-ray therethrough.

At the outside of the X-ray window 21 is provided a spectrometer 70 for rendering the X-ray 20 in parallelism. The spectrometer 70 is formed from a crystal plate made of at least one selected from the group consisting of silicon, lithium fluoride (LiF), graphite, germanium and quartz or an X-ray multilayered film reflecting plate.

The crystal plates can have the function of X-ray surface reflective type crystal plate and/or the function of X-ray transmission type crystal plate. Also, if the crystal plate is made of cubic crystal such as LiF, there are a lot of pairs of identical reflection planes which are perpendicular one another. Therefore, if such a crystal plate is employed, only the crystal plate can render the X-ray 20 in parallelism. In this point of view, if the crystal plate is employed by itself or in the combination with another crystal plate, the thus obtained X-ray with parallelism can be rendered an monochromatic X-ray with parallelism.

The X-ray multilayered reflective film plate is formed such that a few kinds of material are laminated so that a monochromatic X-ray ($\lambda$) with a predetermined wavelength range ($\Delta\lambda$) can be obtained through the diffraction of X-ray. In this case, the relation between the wavelength and reflective angle of the X-ray to be generated is determined by the periodic length of multilayered film reflective plate for the x-ray. If the number of layers and/or the layer periodicity of the multilayered film reflective plate for X-ray is varied, the width of the X-ray wavelength can be varied.

Moreover, two or more crystal plates may be employed. In this case, some components with unnecessary wavelengths of the X-ray can be removed. The crystal plates may be similar crystal plates, but may be different crystal plates.

The electron beam source 3 in FIG. 1 may be any type of electron beam source in dependence on the use thereof. In the case that the X-ray generating apparatus as illustrated in FIGS. 1 and 2 is employed for medical use. For example, the X-ray with parallelism 40 is finally required to have the irradiation area in the order of several centimeters through several ten centimeters. It is desired to employ an anode containing tube type electron beam source and it is also desired to employ a triode tube type source to produce a pulse X-ray. A predetermined voltage is supplied to the electron beam source 3 from the high voltage introducing section 31.

Then, the X-ray generating method using the X-ray generating apparatus illustrated in FIGS. 1 and 2 will be explained below. As described above, the cooling water is introduced from the inlet 16, and the rotating anticathode 1 is rotated around the rotating axis at high speed and moved repeatedly along the rotating axis as occasion demands by the driving motor 5. At the same time, the electron beams 30 is irradiated onto the electron beam irradiating portion 11a of the anticathode 1 from the cathode, thereby generating the X-ray 20. In this case, the intensity of the electron beams 30 is set to a one which can melt the electron beam irradiating portion 11a at least partially or entirely.

When the electron beams 30 with intensity high enough to melt the electron beam irradiating portion 11a at least partially is irradiated, the portion 11a can be heated to a temperature in the vicinity of the melting point thereof (e.g., the melting point of W). As a result, an X-ray with high intensity can be generated from the rotating anticathode 1 (electron beam irradiating portion 11a).

Also, when the electron beams 30 with intensity high enough to melt the surface of the electron beam irradiating portion 11a entirely is irradiated, electron beam irradiating portion 11a of anticathode 1 can be flattened continuously so that the electron beam irradiating portion 11a of the rotating anticathode 1 can have the plane surface during the irradiation of electron beams 30. As a result, the generated X-ray can not be absorbed at the protrusions due to the surface roughness of the electron beam irradiating portion 11a of the rotating anticathode 1 so that the X-ray 20 can be generated stably for a long period of time with maintaining the high intensity of the X-ray 20.

In this embodiment, the surface roughness of the electron beam irradiating portion 11a of rotating anticathode 1 can be reduced to 1 µm or below as the surface average roughness, and particularly 100 nm or below as the surface average roughness under the very large centrifugal force (rotation speed: 12,000 rpm, diameter of anticathode: 280 mm). In other words, in this embodiment, the surface of the electron beam irradiating portion 11a of the rotating anticathode 1 can be maintained flat for a long period of time. In a conventional technique, in contrast, the surface roughness of the rotating anticathode will be increased to a range of 2-10 µm after long use. Therefore, it is apparent from this embodiment that the intended X-ray with high intensity can be generated stably for a long period of time due to the small surface roughness.

In this embodiment, since the electron beam irradiating portion 11a is positioned at the inner wall of the cylindrical portion 11 of the anticathode 1, the inner wall may be melted at least partially by the irradiation of the electron beams. However, since the electron beam irradiating portion 11a is positioned against the centrifugal force from the rotation of the rotating anticathode 1, the melted portions of the inner wall can not be splashed outside.

In this embodiment, a special process is not carried out for the cylindrical portion 11a of the rotating anticathode 1 so that the electron beam irradiating portion 11a is positioned on the inner wall of the cylindrical portion 11 under the condition that the side wall of the cylindrical portion 11 is set parallel to the rotation axis. However, the inner wall of the cylindrical portion 11 can be inclined by several tenths of one degree (some second) through several degrees.

Concretely, the inner wall of the cylindrical portion 11 can be inclined inwardly toward the rotating axis by several tenths of one degree through several degrees. In this case, the electron beam irradiating portion 11a, even though melted, the outer splash of the electron beam irradiating portion 11a can be prevented more effectively.

In contrast, the inner wall of the cylindrical portion 11 can be inclined outwardly from the rotation axis by several tenths of one degree through several degrees. In this case, the intended X-ray can be taken easily out of the apparatus under the condition that the outer splash of the electron beam irradiating portion 11a melted can be prevented.

If the electron beam irradiating portion 11a is formed such that the cross sectional shape becomes a V-shaped ditch or a U-shaped ditch, the outer splash of the electron beam irradiating portion 11a can be prevented more effectively. In this case, the width and depth of the V-shaped ditch or the U-shaped ditch are determined so that the intended X-ray can be taken easily out of the apparatus.

In addition, if the electron beam irradiating portion 11a is made of a target material in dependence on the wavelength of characteristic X-ray to be generated and the area around the electron beam irradiating portion 11a is made of a material with higher melting point and/or higher thermal conductivity than the target material, the cooling efficiency of the anticathode 1 can be enhanced entirely so that the anticathode 1 can not be deformed. In this case, the intended X-ray can be generated constantly over a prolonged period of time.

Furthermore, the anticathode 11, particularly the cylindrical portion 11a to which the electron beams 30 is irradiated, may be made of the target material and the high melting point and/or high thermal conductivity substance may be provided at the backside of the target material so that the inside of the cylindrical portion 11 can be a double structure. In this case, while the intended X-ray is generated by the irradiation of the electron beams 30 onto the cylindrical portion 11, which is cooled by a cooling medium, so that the electron beams 30 can not penetrate through the cylindrical portion 11a on the synergy effect of the large heat resistance and the large cooling effect which are originated from the high melting point and/or the high thermal conductivity of the substance provided at the backside of the target material. As a result, the cooling medium can not be leaked.

As the cooling medium can be exemplified a cooling water and a cooling oil.

The X-ray 20 generated from the rotating anticathode 1 (cylindrical portion 11a) is introduced into a spectrometer 70 so that the intended X-ray 41 with parallelism, which is extracted from the X-ray 20, can be obtained. In this case, the X-ray 41 includes components within a given wavelength range. Therefore, when the X-ray 41 with parallelism is employed for medical use, a given diseased part can be imaged at high resolution under low dosage exposure due to the parallelism and narrow wavelength width intended of the X-ray 41. As described above, since the intensity (brightness) of the X-ray 20 is strong, the intensity of the X-ray 41 is also strong. As a result, a moving object such as coronary artery can be imaged on the synergy effect of the high resolution by the high parallelism of the X-ray 41 and high intensity of the X-ray 41 by the exposure in a short period of time.

In this embodiment, since the electron beam irradiating portion 11a is melted, the metallic vapor pressure may increase by the melting of the target material in the anticathode chamber 2, thereby contaminating the X-ray transmitting window 22. In this case, a rolled protective film, which is made of Ni, BN, Al or mylar against recoiled electrons and exchangeable, may be provided in front of the X-ray transmitting window 22. The rolled protective film is tensed between the supplying roll and the winding roll which are provided inside the X-ray window 21. The thickness of the protective film is appropriately adjusted in view of the recoil electron energy and the X-ray absorption.

In this embodiment, although the electron beam is employed as the energy beam, another energy beam such as laser beam and ion beam may be employed.

In this embodiment, the back side 11a of the cylindrical portion 11 may be made some material such as stainless steel, Mo, Cu.

In this embodiment, although the rotating anticathode is employed, a planer anticathode may be employed when the electron beam irradiating portion is not melted, thereby generating the X-ray with not high intensity.

Figure 3:
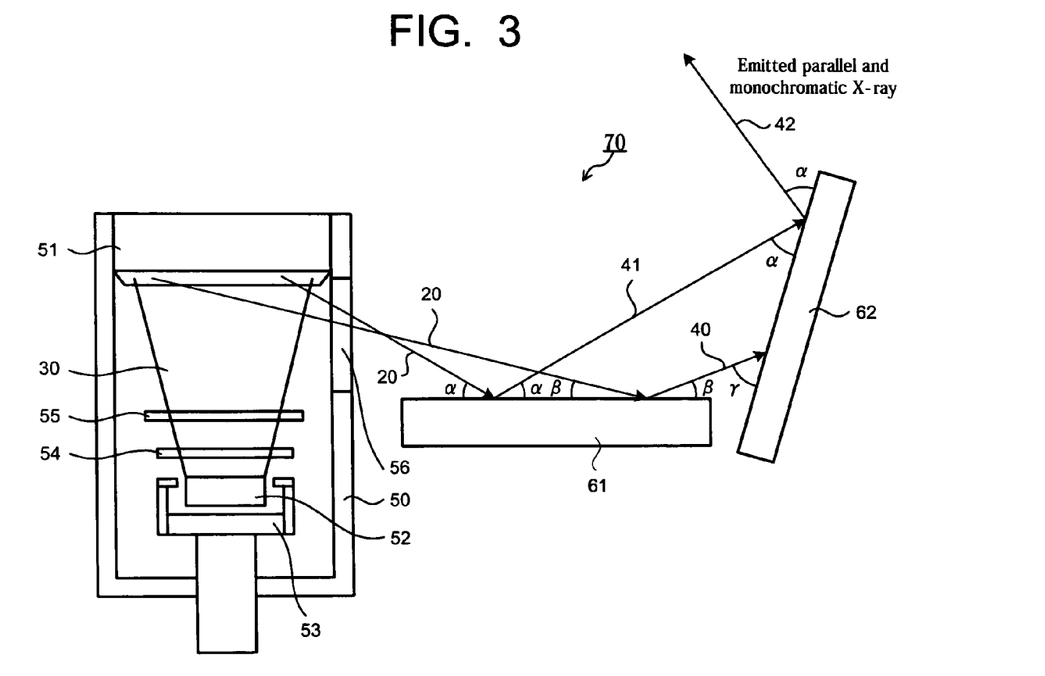
FIG. 3 is a structural view illustrating another X-ray generating apparatus according to the present invention.

FIG. 3 is a structural view illustrating another X-ray generating apparatus using a stationary and planer target. The same reference numerals are imparted to like components throughout FIGS. 1-3. In this case, an X-ray with large irradiating area can be generated so that the structure of the spectrometer to be used is important. In this point of view, in this embodiment, the structure of the spectrometer will be described in detail.

In the X-ray generating apparatus illustrated in FIG. 3, an anticathode 51 is disposed in a vacuum chamber 50, and a cathode 52 is disposed opposite to the anticathode 51. The cathode 52 is fixed inside the wehnelt 53 via an insulating material such as ceramic material. A given voltage is applied between the cathode 52 and the wehnelt 53 so that the wehnelt 53 functions as a lens for electron beams.

An aperture grid 54 and an anode 55 are provided between the anticathode 51 and the cathode 52. The electric potential of the aperture grid 54 can be varied within a range of ±7 kV for the cathode 52 in accordance with various conditions. If the electric potential of the aperture grid 54 is set negative for the cathode 52, the electron beams is cut off. If the electric potential of the aperture grid 54 is set positive for the cathode 52, the space charge from the cathode 52 can be compensated so that electrons can be extracted from the cathode 52. According to the aperture grid 54, in this embodiment, the current of the electron beams can be varied by controlling the aperture grid 54 voltage. According to the anode 55, the electron beams 30 emitted from the cathode 52 can be accelerated by the electric potential between the cathode 52 and the anode 55. After passing though anode, the electron beams 30 travel with no electronic potential field to the anticathode 51. Thus, the influence of the high temperature of the target can be reduced by the anode 55. When the anode 55 is not essential, the anode 55 may be omitted. In this embodiment, shown in FIGS. 3 and 4, since the cathode 52, the aperture grid 54 and the anode 55 are provided, namely, the X-ray generator constitutes a triode type. At the vacuum chamber 50 is provided an X-ray transmission window 56 through which the X-ray 20 generated from the anticathode 51 can be taken out of the chamber.

Normally, the grid is formed in mesh type produce shorter than msec pulse electron beam with high efficiency, but in this embodiment, if the grid is formed in mesh, the electron beams can not be irradiated uniformly onto the anticathode 51 and the mesh is heated by electric current and damaged easily when it is used to produce longer pulse, especially direct current. For example, the electron beams passing through the openings of the grid can be irradiated sufficiently onto the anticathode 51, but the electron beams collided with the lines of the grid can not be irradiated sufficiently onto the anticathode 51. In this point of view, in this embodiment, the grid is formed in a circle type so that the electron beams 30 can pass through the opening inside the circular grid. In this way, the circular grid is called as the aperture grid.

In this embodiment, other parts such as the anticathode 51 and vacuum chamber 50 except the X-ray transmission window 56 of the X-ray generating apparatus is cooled with insulating oil. However, a pipe may be attached to the part to be cooled such as the anticathode 51. In this case, a cooling medium is circulated in the pipe. An advantage of circulated type is that the anticathode 51 can be set in the vacuum chamber 50 entirely under not deformation by the pressure from outside.

Then, a first crystal plate 61 and a second crystal plate 62 are provided by a given angle outside of the X-ray transmission window 56 at the vacuum chamber 50.

In the X-ray generating apparatus illustrated in FIG. 3, the current of the electron beams 30 generated from the cathode 52 is controlled by the grid 54, and then, the electron beams 30 is accelerated by the anode 55. In this way, the accelerated electron beams 30 is irradiated onto the anticathode 51 under the condition that the current of the electron beams 30 is controlled appropriately so that the X-ray 20 (of white and non-parallelism) can be generated. Then, the X-ray 20 is taken out of the X-ray transmission window 56, and the X-ray 20 is reflected at the first crystal plate 61 (transmission type) which is made of cubic crystal such as LiF and the reflected X-ray 41 is subsequently reflected by the second crystal plate 62 which is made of any kind of crystal, so that the monochromic X-ray with parallelism is generated. Herein, since the X-ray can be an X-ray with parallelism after the reflection at the first transmission type crystal plate 61.

In this embodiment, since the first crystal plate 61 and the second crystal plate 62 are employed, some components with unnecessary wavelength can be removed from the X-ray 20. For example, since the incident angle ($\alpha$) of the X-ray 20 and the reflective angle ($\alpha$) of the X-ray 41 at the first crystal plate 61 are the same as the incident angle and the reflective angle at the second crystal plate 62 where the angle between first and second crystal reflection planes is arranged to be $2\alpha$, the incident angle of the X-ray 41 to the second crystal plate become $\alpha$. This means the X-ray 41 can be reflected at the second crystal plate 62, and thus, irradiated onto an object (In FIG. 3, the incident angle and the reflective angle are designated by reference character "$\alpha$"). However, the X-ray 40 with a different wavelength from the X-ray 41 is incident onto and reflected from the first crystal plate 61 by the angle "$\beta$", and then, incident onto the second crystal plate 62 by the angle "$\gamma$". In this case, since the incident angle "$\gamma$" of the X-ray 40 for the second crystal plate 62 is different from the reflective angle "$\beta$" for the first crystal plate 61, the X-ray 40 can not be reflected from the second crystal plate 62.

In this embodiment, instead of using the first crystal plate 61 is made of cubic crystal such as LiF, the first crystal plate 61 may be formed by combining two crystal plates so that the reflection planes of the crystal plates can be orthogonal to one another.

The crystal plates may be made of at least one selected from the group consisting of silicon, lithium fluoride (LiF), graphite, germanium and quartz.

Then, a modified X-ray generating apparatus using stationary and the planer target was explained. The same reference numerals are imparted to like components throughout FIGS. 1-4. In this embodiment, the X-ray generator is constructed as the one illustrated in FIG. 3, and only the spectrometer is different from the one illustrated in FIG. 3.

Figure 4:
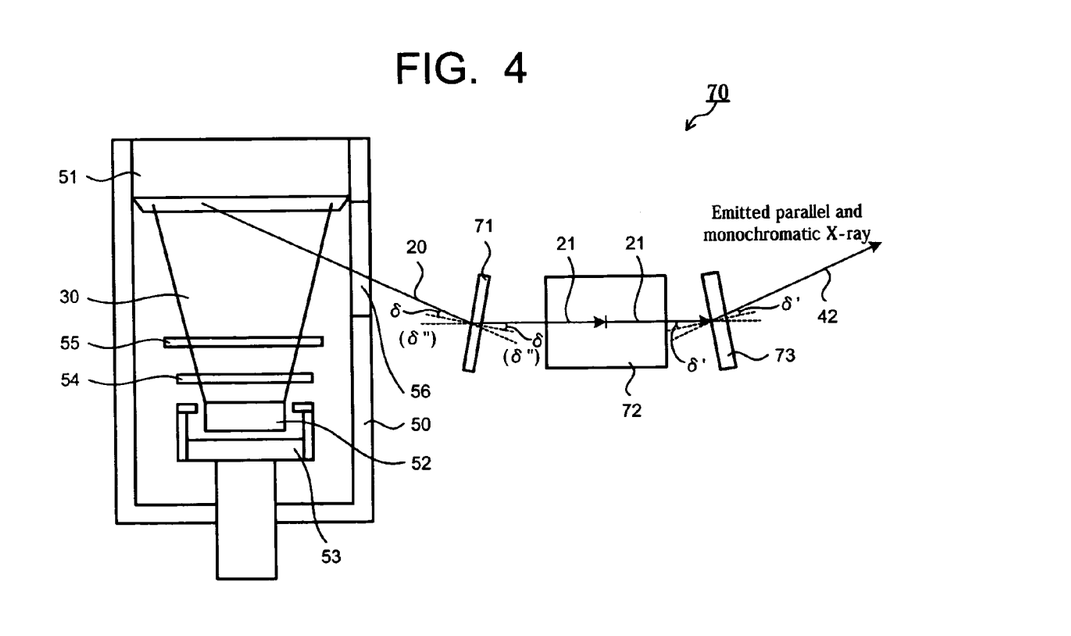
FIG. 4 is a structural view illustrating a modified X-ray generating apparatus from the one illustrated in FIG. 3.

In FIG. 3, the spectrometer consists of two type crystal plates, namely, transmission "Laue" type 61 and reflective type 62. In FIG. 4 relating to this embodiment, however, the spectrometer consists of two X-ray transmission type (Laue type) crystal plates 71, 73 and one X-ray surface reflective type crystal plate 72. As illustrated in FIG. 4, these crystal plates are arranged subsequently by the numerical order from the X-ray generator.

The reflection plane of the second crystal plate 72 is set almost parallel to the page space so that the X-ray is reflected forward for the page space. The reflection plane of the first crystal plate 71 and the third crystal plate 73 are set almost perpendicular to the page space. Therefore, the reflection plane of the second crystal plate 72 is set almost perpendicular to the reflection plane of the first crystal plate 71 and the third crystal plate 73. The d (111) reflection plane of Si may be applied for the first crystal plate 71 and the second crystal plate 72, and the d' (200) reflection plane of Si may be applied for the third crystal plate 73. In this case, although the spacing of d and d' are different from one another, the crystal plates are arranged so that the relations of 2d sin $\delta$=$\lambda$ and 2d' sin $\delta$'=$\lambda$ can satisfied for the different incident angles $\delta$ and $\delta$' which correspond to the first and second crystal plates 71, 72 for the former equation and the third crystal plate 73 for the latter equation, for the X-ray with wavelength $\lambda$.

In this embodiment, the X-ray 20 (of white and non-parallelism) with a large irradiating area is taken out of the X-ray transmission window 56, and the incident beams travel onto the first crystal plate 71 by the angle $\delta$ as shown in FIG. 4, and also by the angle $\delta$ downward to the page space, (however this angle is not shown in the figure) so as to set the diffraction plain of the second crystal plane be nearly parallel to the page space. In this case, the X-ray 20 is diffracted in accordance with the Bragg's equation 2d sin $\delta$=$\lambda$ through the first crystal plate 71. Not demonstrated clearly, if another X-ray with a different wavelength $\lambda$' satisfies the Bragg's equation when the incident X-ray beams travel onto the first crystal plate 71, the X-ray can pass through the first crystal plate 71 after diffraction. In this point of view, even though the X-ray 20 passes through the first crystal plate 71, the X-ray 20 remains the inherent white X-ray with non-parallelism.

Since the X-ray 20 with a wavelength $\lambda$ has a larger irradiating area, the thus obtained X-ray through the first crystal plate 71 has some components parallel to the plane which has an angle of $\delta$ from the page space and other components non-parallel to the plane. Since the diffracting direction of the X-ray with a wavelength $\lambda$ ' is different from the diffracting direction of the X-ray with the wavelength $\lambda$, the X-ray with the wavelength $\lambda$' can not be parallel to the X-ray with the wavelength $\lambda$.

Then, the X-ray 20 is incident onto the second crystal plate 72 after passing through the first crystal plate 71, and then, reflected forward for the page space. The thus obtained reflected X-ray is incident onto the third crystal plate 73 by an angle of $\delta$' so that the parallel components of the X-ray can be taken out satisfying the Bragg's equation for the third crystal plate 73. In this way, the monochromatic X-ray 41 with parallelism can be obtained from the white X-ray 20 with non-parallelism.

Only if the X-rays with the wavelengths $\lambda$ and $\lambda$' can be selected by the rotation of the only third crystal plate 73 to satisfy the Bragg's equation, and thus the intended X-ray with parallelism can be obtained from the X-rays. In other words, from a plurality of X-rays with parallelism and respective different wavelengths, aimed monochromatic X-ray with parallelism can be obtained using only the third crystal plate 73 rotation. When the change of the wavelength of the X-rays is very large, the area of the X-ray with parallelism may be decreased. In this case, it can be recovered by the rotationally readjustment of all three crystal plates.

Although the present invention was described in detail with reference to the above examples, this invention is not limited to the above disclosure and every kind of variation and modification may be made without departing from the scope of the present invention.

Concretely, in the embodiments relating to FIGS. 1-4, a film (coating) may be provided on the surface of the anticathode so as to reduce the evaporation velocity of the electron beam irradiating portion. The film may be made of a material selected from the group consisting of BN, graphite, diamond, Be and alumina $Al_2O_3$.

What is claimed is:

1. A method for generating an X-ray, comprising the steps of:
    irradiating an energy beam onto a target from an energy beam source, thereby generating an X-ray with an irradiating area to be irradiated onto an object; and
    introducing said X-ray into a spectrometer including a first reflective crystal plate and a second reflective crystal plate which are subsequently arranged at a relative angle twice as large as an incident angle of said X-ray onto said first reflective crystal plate, thereby generating an X-ray with parallelism through the selection of wavelength and wavelength range.

2. The generating method as defined in claim 1, wherein said first reflective crystal plate and said second reflective crystal plate are made of a material selected from the group consisting of silicon, lithium fluoride (LiF), graphite, germanium and quartz.

3. The generating method as defined in claim 1, further comprising the step of, before introducing said X-ray into said spectrometer, transmitting said X-ray through at least one of an absorptive plate and a slit so as to remove components with unnecessary wavelength of said X-ray.

4. The generating method as defined in claim 3, wherein said absorptive plate is an aluminum plate.

5. The generating method as defined in claim 1, wherein said target is a stationary type target.

6. The generating method as defined in claim 1, wherein said energy beam source is an electron beam source so that said energy beam can be an electron beam.

7. The generating method as defined in claim 6, wherein said electron beam source is a diode or a triode type electron beam source.

8. The generating method as defined in claim 1, wherein said X-ray with parallelism is usable for medical use.

9. An apparatus for generating an X-ray, comprising:
    a target for generating an X-ray through the irradiation of an energy beam;
    an energy beam source for generating said energy beam to generate said X-ray so as to have an irradiating area to be irradiated onto an object; and
    a spectrometer for selecting wavelength and wavelength range of said X-ray through the introduction of said X-ray so as to generate an X-ray with parallelism from said X-ray,
    wherein said spectrometer includes a first reflective crystal plate and a second reflective crystal plate which are subsequently arranged at a relative angle twice as large as an incident angle of said X-ray onto said first reflective crystal plate.

10. The generating apparatus as defined in claim 9, wherein said first reflective crystal plate and said second reflective crystal plate are made of a material selected from the group consisting of silicon, lithium fluoride (LiF), graphite, germanium and quartz.

11. The generating apparatus as defined in claim 9, further comprising at least one of an absorptive plate and a slit so as to remove components with unnecessary wavelength of said X-ray by transmitting said X-ray through said at least one before said X-ray is introduced into said spectrometer.

12. The generating apparatus as defined in claim 11, wherein said absorptive plate is an aluminum plate.

13. The generating apparatus as defined in claim 9, wherein said energy beam source is an electron beam source so that said energy beam can be an electron beam.

14. The generating apparatus as defined in claim 13, wherein said electron beam source is a diode or a triode type electron beam source.

15. The generating apparatus as defined in claim 9, wherein said X-ray with parallelism is usable for medical use.

16. A method for generating an X-ray, comprising the steps of:
    irradiating an energy beam onto a target from an energy beam source, thereby generating an X-ray with an irradiating area to be irradiated onto an object; and
    introducing said X-ray into a spectrometer including a first transmission crystal plate, a second reflective crystal plate and a third transmission crystal plate, which are subsequently arranged so that a reflection plane of said second crystal plate is perpendicular to reflection planes of said first crystal plate and third crystal plate, thereby generating an X-ray with parallelism through the selection of wavelength and wavelength range.

17. The generating method as defined in claim 16, wherein said first reflective crystal plate, said second transmission crystal plate and said third reflective crystal plate are made of a material selected from the group consisting of silicon, lithium fluoride (LiF), graphite, germanium and quartz.

18. The generating method as defined in claim 16, further comprising the step of, before introducing said X-ray into said spectrometer, transmitting said X-ray through at least one of an absorptive plate and a slit so as to remove components with unnecessary wavelength of said X-ray.

19. The generating method as defined in claim 18, wherein said absorptive plate is an aluminum plate.

20. The generating method as defined in claim 16, wherein said target is a stationary type target.

21. The generating method as defined in claim 16, wherein said energy beam source is an electron beam source so that said energy beam can be an electron beam.

22. The generating method as defined in claim 21, wherein said electron beam source is a diode or a triode type electron beam source.

23. The generating method as defined in claim 16, wherein said X-ray with parallelism is usable for medical use.

24. An apparatus for generating an X-ray, comprising:
    a target for generating an X-ray through the irradiation of an energy beam;
    an energy beam source for generating said energy beam to generate said X-ray so as to have an irradiating area to be irradiated onto an object; and
    a spectrometer for selecting wavelength and wavelength range of said X-ray through the introduction of said X-ray so as to generate an X-ray with parallelism from said X-ray, said spectrometer including a first transmission crystal plate, a second reflective crystal plate and a third transmission crystal plate which are subsequently arranged so that a reflection plane of said second crystal plate is perpendicular to reflection planes of said first crystal plate and said third crystal plate.

25. The generating apparatus as defined in claim 24, wherein said first reflective crystal plate, said second transmission crystal plate and said third reflective crystal plate are made of a material selected from the group consisting of silicon, lithium fluoride (LiF), graphite, germanium and quartz.

26. The generating apparatus as defined in claim 24, further comprising at least one of an absorptive plate and a slit so as to remove components with unnecessary wavelength of said X-ray by transmitting said X-ray through said at least one before said X-ray is introduced into said spectrometer.

27. The generating apparatus as defined in claim 26, wherein said absorptive plate is an aluminum plate.

28. The generating apparatus as defined in claim 24, wherein said energy beam source is an electron beam source so that said energy beam can be an electron beam.

29. The generating apparatus as defined in claim 28, wherein said electron beam source is a diode or triode type electron beam source.

30. The generating apparatus as defined in claim 24, wherein said X-ray with parallelism is usable for medical use.

* * * * *